United States Patent
Breuer et al.

(10) Patent No.: US 9,606,199 B2
(45) Date of Patent: Mar. 28, 2017

(54) MR-COMPATIBLE BLOOD SAMPLING SYSTEM FOR PET IMAGING APPLICATIONS IN COMBINED PET/MR IMAGING SYSTEM

(75) Inventors: Johannes Breuer, Dortmund (DE);
Ronald Grazioso, Knoxville, TN (US);
James Corbeil, Knoxville, TN (US);
Nan Zhang, Knoxville, TN (US);
Matthias J. Schmand, Lenoir City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2380 days.

(21) Appl. No.: 12/260,966

(22) Filed: Oct. 29, 2008

(65) Prior Publication Data

US 2009/0108206 A1    Apr. 30, 2009

Related U.S. Application Data

(60) Provisional application No. 60/983,325, filed on Oct. 29, 2007.

(51) Int. Cl.
- *G01R 33/28* (2006.01)
- *A61B 5/15* (2006.01)
- *G01R 33/48* (2006.01)
- *G01T 1/16* (2006.01)

(52) U.S. Cl.
CPC ........ *G01R 33/28* (2013.01); *A61B 5/150992* (2013.01); *G01R 33/481* (2013.01); *G01T 1/1603* (2013.01)

(58) Field of Classification Search
CPC ...... G01R 33/481; G01R 33/28; G01T 1/1603
USPC ................ 250/363; 600/407, 410, 411, 436; 324/318
See application file for complete search history.

(56) References Cited

U.S. PATENT DOCUMENTS

| | | | |
|---|---|---|---|
| 2003/0107000 A1* | 6/2003 | Yamashita et al. | 250/363.03 |
| 2006/0025673 A1* | 2/2006 | De Leon et al. | 600/410 |
| 2007/0299335 A1* | 12/2007 | Declerck et al. | 600/420 |

OTHER PUBLICATIONS

Sepideh Shokouhi, A Non-invasive LSO-APD Blood Radioactivity Monitor for PET Imaging Studies, Nov. 10, 2002. IEEE.*
Ronald Grazioso, APD-based PET detector for simultaneous PET/MR imaging, Nuclear Instruments and Methods in Physics Research A 569 (2006) 301-305.*
J. Breuer, MR-Compatible Blood Sampler for PET, 2007 IEEE Nuclear Science Symposium Conference Record.*

(Continued)

*Primary Examiner* — Serkan Akar

(57) ABSTRACT

An automated blood sampling system for PET imaging applications that can be operated in or very near to the field of view (FOV) of an MR scanner, such as in a combined MR/PET imaging system. A radiation detector uses APDs (avalanche photo-diodes) to collect scintillation light from crystals in which the positron-electron annihilation photons are absorbed. The necessary gamma shielding is made from a suitable shielding material, preferably tungsten polymer composite. Because the APDs are quite small and are magnetically insensitive, they can be operated in the strong magnetic field of an MR apparatus without disturbance.

14 Claims, 5 Drawing Sheets

(56) References Cited

OTHER PUBLICATIONS

D. Schlyer, Development of a Simultaneous PET/MRI Scanner, Nov. 2, 2004. IEEE.*
Nobuyuki Kudomi, Development of a GSO Detector Assembly for a Continuous Blood Sampling System, IEEE, Transactions on Nuclear Science, vol. 50, No. 1, Feb. 2003.*

* cited by examiner

MR-COMPATIBLE BLOOD SAMPLING SYSTEM FOR PET IMAGING APPLICATIONS IN COMBINED PET/MR IMAGING SYSTEM

CLAIM OF PRIORITY FROM RELATED APPLICATIONS

This application claims priority under 35 U.S.C. §119(e) from provisional application Ser. No. 60/983,325 filed Oct. 29, 2007.

FIELD OF THE INVENTION

The present invention generally relates to the field of medical imaging, and systems for obtaining diagnostic images such as nuclear medicine images and magnetic resonance (MR) images. In particular, the present invention relates to improvements in automated blood-sampling systems to provide such a system that is compatible for use with multiple modality imaging systems that produce nuclear medicine images from positron emission tomography (PET) data and magnetic resonance imaging (MRI) data.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred.

On the other hand, Magnetic Resonance Imaging (MRI) is primarily used for obtaining high quality, high resolution anatomical and structural images of the body. MRI is based on the absorption and emission of energy in the radio frequency range primarily by the hydrogen nuclei of the atoms of the body and the spatial variations in the phase and frequency of the radio frequency energy being absorbed and emitted by the imaged object. The major components of an MRI imager include a cylindrical magnet, gradient coils within the magnet, an RF coil within the gradient coil, and an RF shield that prevents the high power RF pulses from radiating outside of the MR imager, and keeps extraneous RF signals from being detected by the imager. A patient is placed on a patient bed or table within the magnet and is surrounded by the gradient and RF coils.

The concept of merging PET and MR imaging modalities into a single device is generally known in the art. See, e.g., U.S. Pat. No. 4,939,464, incorporated herein by reference in its entirety. See also copending U.S. application Ser. No. 11/532,665 assigned to the same assignee herein. Recently, there has been increased interest and research in using this combined modality to provide accurate functional and structural quantitative images for applications such as diagnosis of stroke patients, oncology, brain mapping and Alzheimer's research.

In order to quantify the uptake of administered PET tracers by the investigated organs it is necessary to measure the amount of radioactivity in arterial blood. Consequently, an important device that is used for functional imaging with PET is an automated Blood Sampler—a device that measures the specific amount of radioactivity per blood volume in the artery over time. This information is used in the calculation of a 3D map of the metabolic rate in the observed region of the patient, test person or test animal.

Conventional blood samplers have the following basic design. A pump draws blood from an artery of the observed person or animal at a constant pump speed. This arterial blood is conveyed via a catheter through an arrangement of PET scintillator crystals (such as BOO, GSO or LSO). If positron decay occurs in the catheter, the emitted positron will annihilate with an electron in its direct proximity. Thus, two annihilation photons emerge with a definite energy of 511 keV. The PET scintillation crystals surround the catheter in such a way that it is very likely that both photons will be absorbed and translated into scintillation photons. The scintillation light is collected usually by photomultiplier tubes (PMTs) that are attached to the crystal.

For most applied scintillators, the energy of the absorbed particles is proportional to the amount of generated scintillation light. Suitable electronics distinguish between events which actually originate from the catheter within the field-of-view of the blood sampler and background events that may come from the patient or other radioactive sources. For example, this can be achieved by counting only events in which a total energy of around 1022 keV (=2×511 keV) is deposited in the crystals. Another method is coincidence detection. In this method, there are two optically separated crystals on opposite sides of the catheter. An event is counted if both crystals detect a 511 keV photon within a very short time of each other. The timing window is typically in the order of 10 ns.

Since commercially available automated blood sampling systems cannot be operated in the strong magnetic field of MR scanners, there exists a need in the art for a new blood sampler that is MR-compatible, such that an MR/PET multimodality imaging system may be used to its full potential.

SUMMARY OF THE INVENTION

The present invention provides a solution to the existing need in the art, by providing an automated blood sampler for PET imaging applications that can be operated in or very near to the field of view (FOV) of an MR scanner, such as in a combined MR/PET imaging system. The invention is based on a radiation detector that uses APDs (avalanche photo-diodes) to collect scintillation light from crystals in which the positron-electron annihilation photons are absorbed. The necessary gamma shielding is made from a suitable shielding material, preferably tungsten polymer composite. Because APDs are quite small and are magnetically insensitive, they can be operated in the strong magnetic field of an MR apparatus without disturbance.

BRIEF DESCRIPTION OF THE DRAWINGS

The invention will now be more fully described by way of example with reference to the accompanying drawings in which.

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

Figure 1:
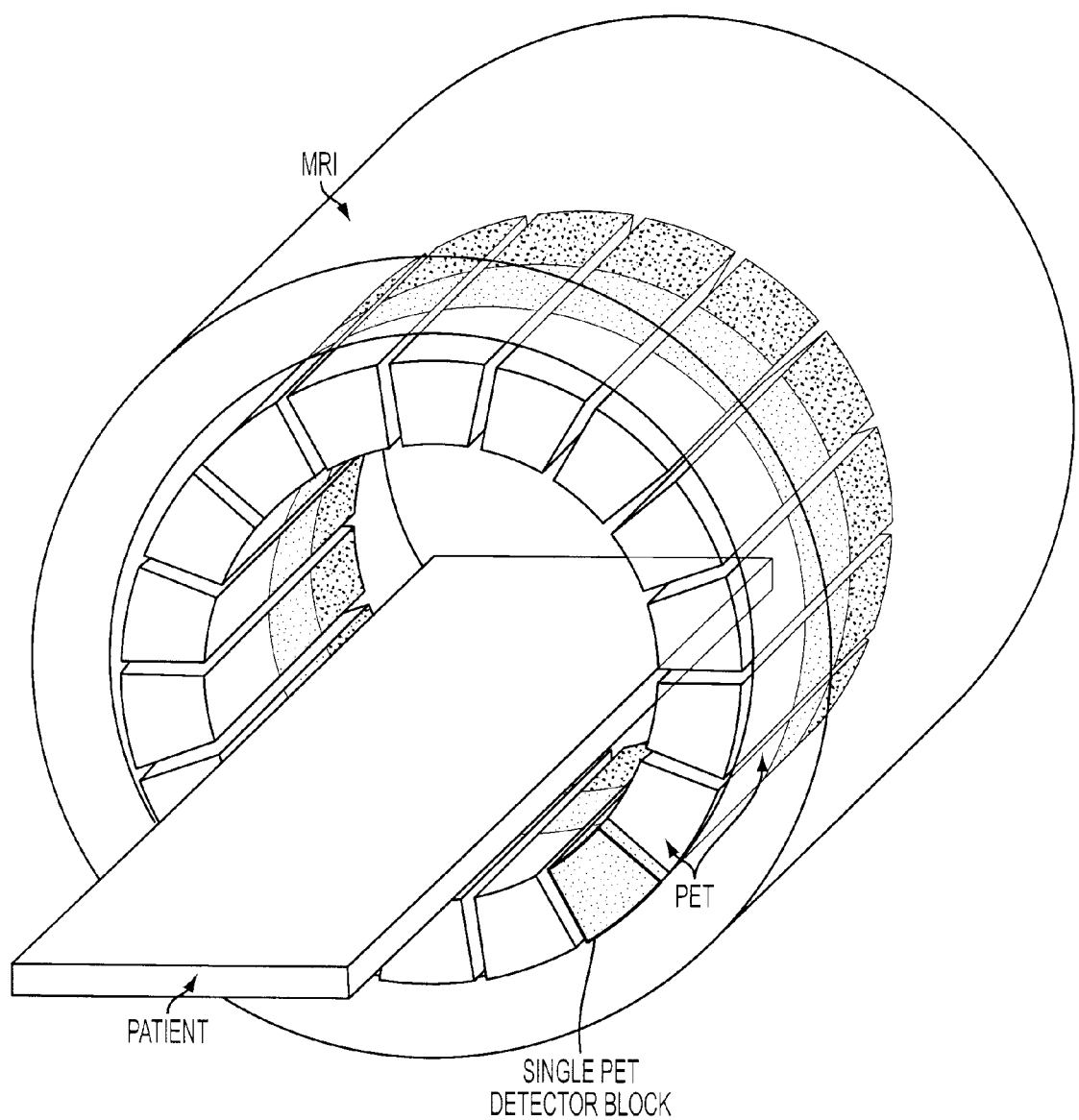
FIG. 1 is a perspective view of a combined PET/MR system which is applicable to the novel blood sampler of the invention, showing a plurality of PET detector rings within an MR field of view.

As shown in FIG. 1, an example combined MR/PET imaging system with which the blood sample of the invention is used, has a plurality of PET detector rings, such as 3 rings, disposed within an MRI magnet. Accordingly, each detector ring has an outer diameter dimensioned to be received within the geometry of the MRI scanner. A patient table or bed is provided to receive a patient to be imaged. PET and MR data acquisitions are carried out on the patient, either simultaneously, in an interlaced or interleaved manner, or sequentially.

Figure 2:
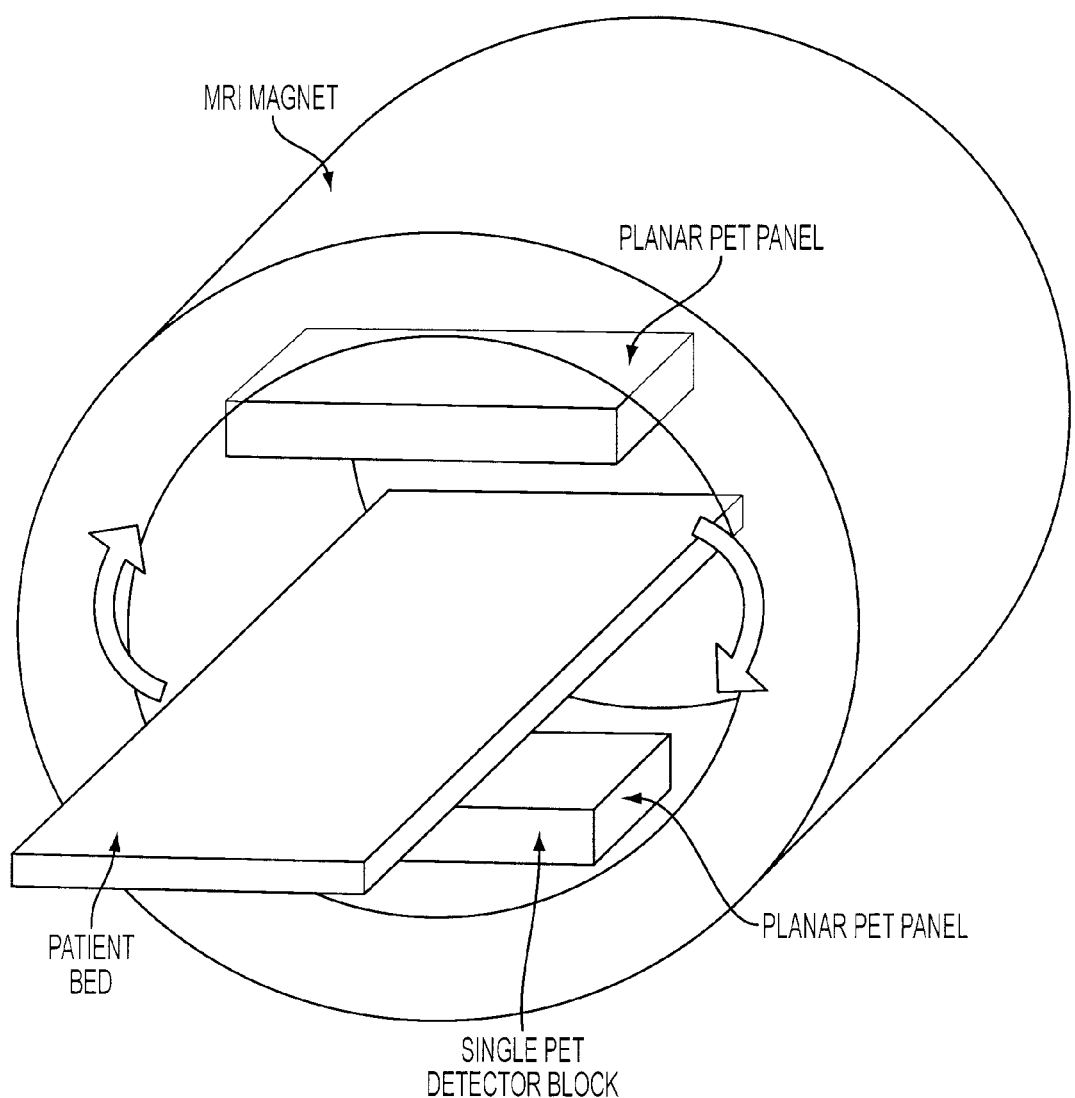
FIG. 2 is a perspective view of an alternate configuration combined PET/MR system which is applicable to the novel blood sampler of the invention, showing a plurality of planar PET detector panels positioned on the end of a MR scanner.

An additional alternate configuration of MR/PET imaging system applicable to the blood sampler of the invention is shown in FIG. 2, wherein two planar PET detector panels are provided and positioned 180° apart within the MR scanner FOV. The PET detector panels also may be positioned at the end of the MR patient gantry outside the FOV. The detector panels may be configured to rotate about the patient, either partially or a full 360°. The detector panels also may be configured to be stationary. In each of the embodiments, the PET detector modules can be either permanently mounted within or on the MRI scanner, or be retractable therefrom. It is noted that the PET detector modules include scintillation crystals and APD photodetectors coupled to the scintillation crystals.

Figure 3:
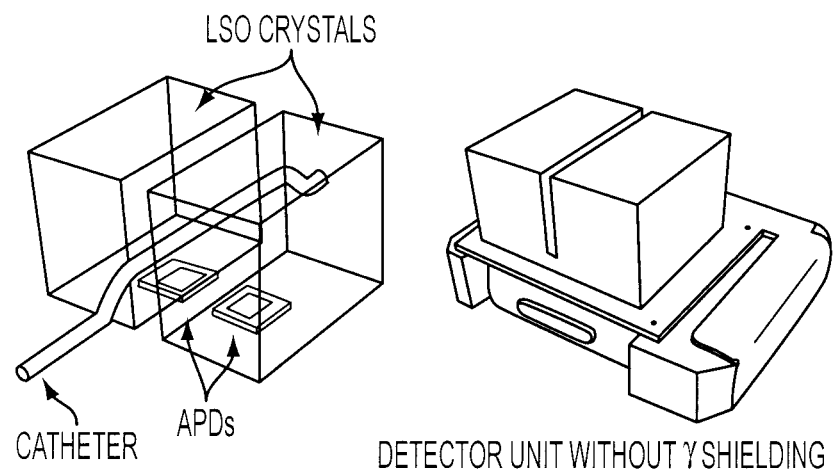
FIG. 3 is a perspective diagram of an MR-compatible blood sampler PET detector unit in accordance with an embodiment of the invention.
Figure 4:
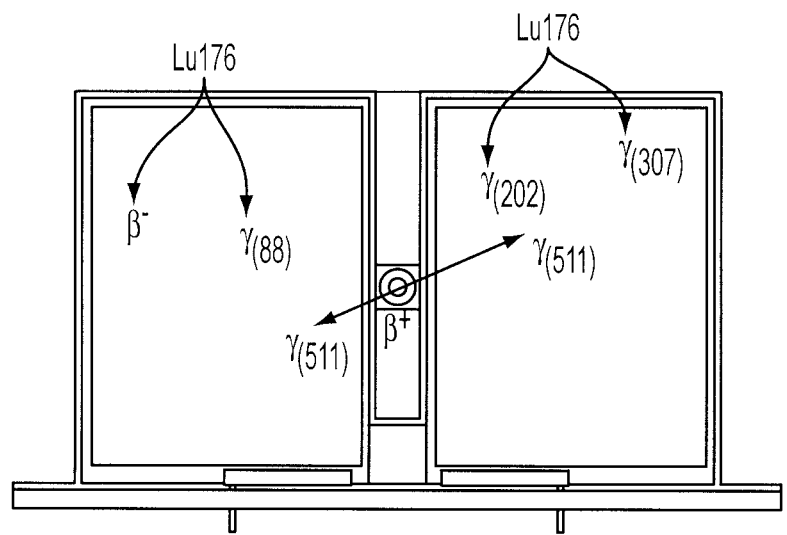
FIG. 4 is a cross-sectional view of the blood sampler PET detector unit as shown in FIG. 3.

FIG. 3 shows an embodiment of a MR-compatible PET blood sampler in accordance with the invention. The blood sampler detector unit, which in operation is placed within or very close to the FOV of the MR scanner, includes two LSO crystal blocks as scintillators and two APD photodetectors attached to the LSO crystal blocks. Scintillation crystals other than LSO also could be used, such as GSO or BGO. A catheter carrying arterial blood of an observed subject passes between the crystal blocks of the detector unit. In the detector unit, the two annihilation photons following a β+ decay are absorbed separately by the LSO crystals (which have typical dimensions of 50×40×30 mm$^3$) that surround the catheter in a sandwich-like geometry as shown. The scintillation light is collected by the two APDs (for example, Hamamatsu S8664-10×10 mm$^2$ APDs) that can be operated in a strong magnetic field such as produced by a MR apparatus (in contrast to PMTs, which cannot function properly in a strong magnetic field). FIG. 4 shows a cross-sectional view of the detector unit shown in FIG. 3.

Figure 5:
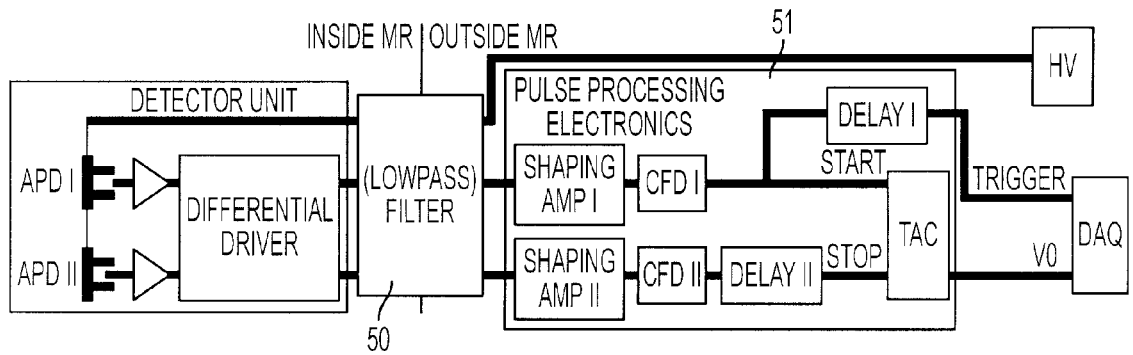
FIG. 5 is a circuit block diagram showing an embodiment of detector processing electronics of the novel MR-compatible blood sampler of the invention.

The APDs convert the collected scintillation light into electric signals. As shown in FIG. 5, the signals are pre-processed by a charge-sensitive amplifier and a differential driver, and then are sent via a cable through a MR filter plate 50 to the outside of the MR FOV, and thus out of the MR magnetic field, and subsequently to pulse processing electronics 51. The amplified and shaped signals are translated into trigger pulses by CFDs (constant fraction discriminators) and fed into a TAC (time-amplitude converter) unit to determine the time difference between both single events. One CFD signal is used as trigger for the DAQ (data acquisition) unit. A high voltage source (HV) is provided for the APDs and other circuit components as may be needed.

The detector has a constant background due to the decay of Lu176 in LSO. Since the β-decay is followed by a gamma cascade with energies of 307, 202, and 88 keV, coincident events can be triggered eventually, if one crystal absorbs the electron and the other crystal absorbs the gammas. The chosen geometry is optimized based on simulations of the interactions of the annihilation photons with the scintillator crystals and the shielding. The signals are pre-amplified and driven through cables to the filter plate of the MR cabinet, where they are filtered in order to minimize noise in the MR cabinet—and to avoid false triggers due to pickup of MR sequences. Coincidence detection electronics outside of the MR cabinet are used to determine qualified events. To reduce detector dead time and background due to random coincidences, the detector unit is surrounded by an MR-compatible gamma ray shielding. For this purpose, a tungsten polymer composite with a density of 11 g/cc can be used.

Figure 6:
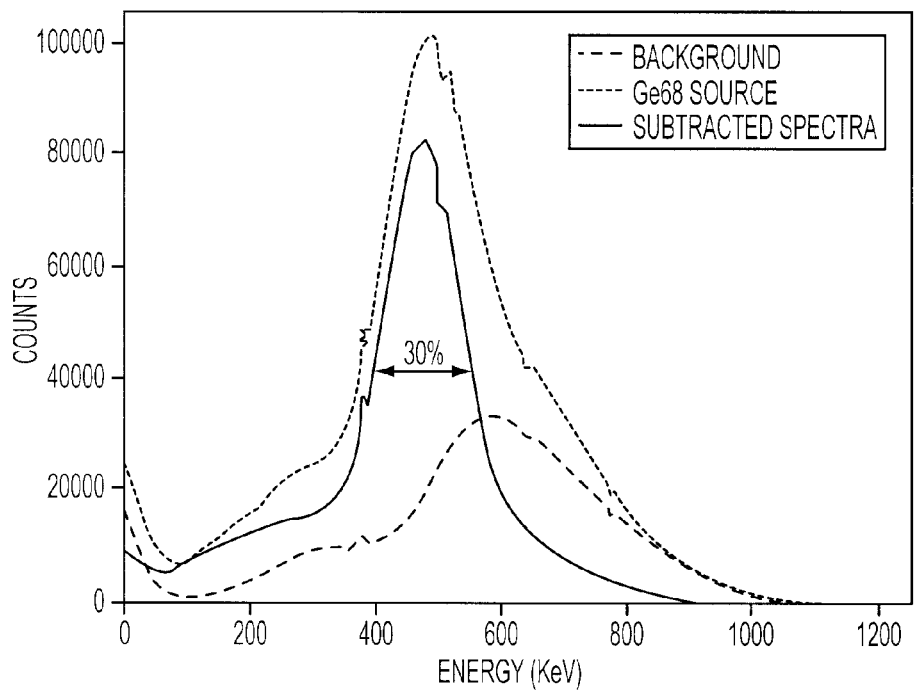
FIG. 6 is a graph showing a single crystal energy spectrum for a 0.8 mCi Ge68 point source, for a scintillation crystal of a blood sampler in accordance with the invention.
Figure 7:
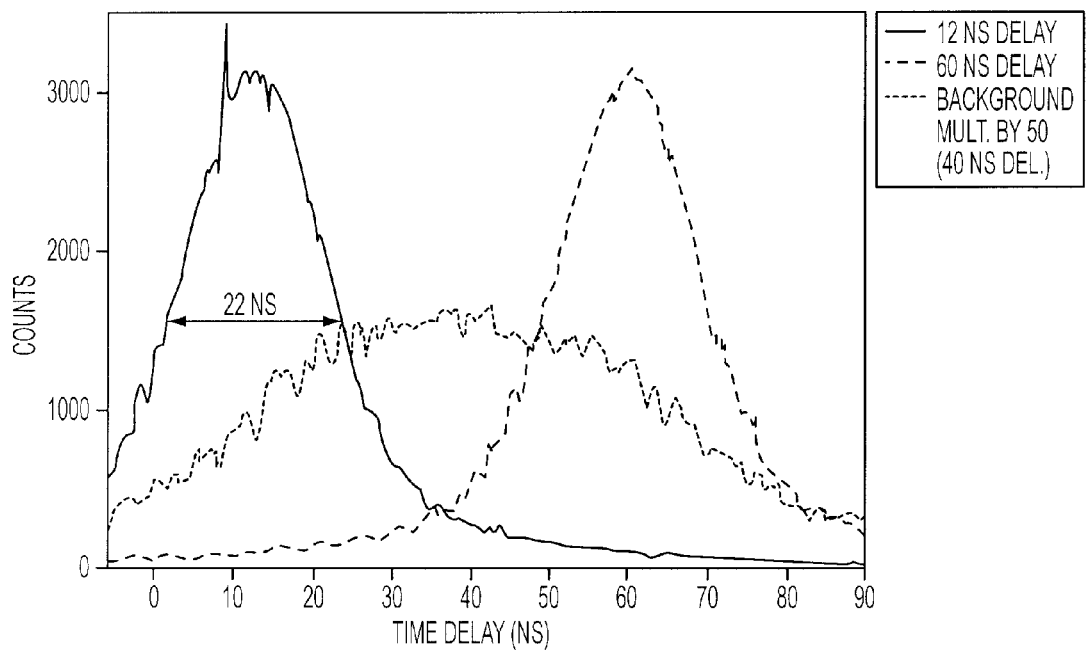
FIG. 7 is a graph showing a timing spectrum of a blood sampler detector in accordance with the invention.
Figure 8:
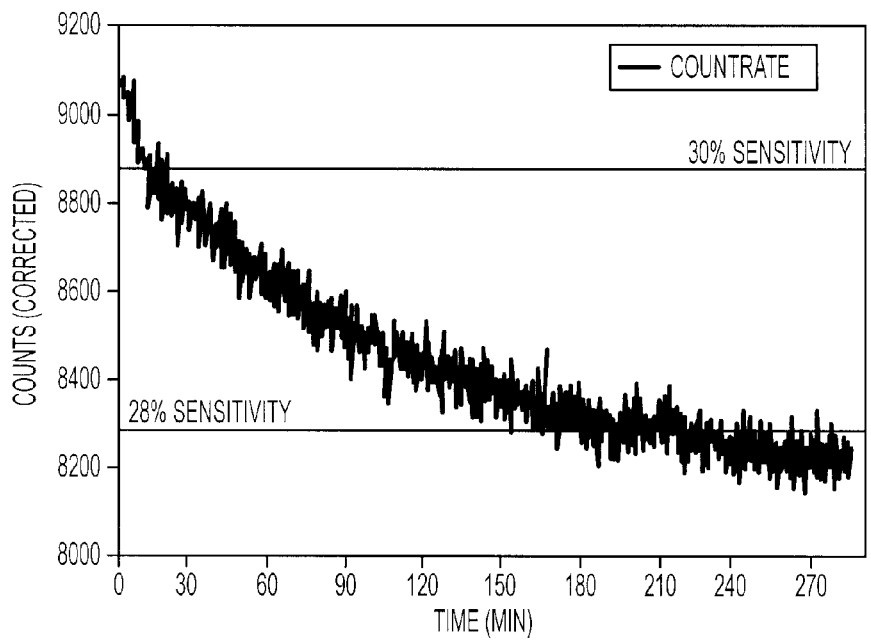
FIG. 8 is a graph showing the count rate for the 0.8 mCi Ge68 point source during warm-up of a blood sampler in accordance with the invention.

A prototype was built with NIM electronics for pulse processing. The single crystal energy spectrum for a 0.8 mCi Ge68 point source is illustrated in FIG. 6 (shaping time: 100 ns). The large background is due to the β-decay of Lu176. After subtraction of the background, the spectrum shows an energy resolution of around 30% FWHM. For further tests, the CFD threshold was set to 200 keV. The time resolution was found to be about 22 ns FWHM (FIG. 7, shaping time: 100 ns). The timing window for coincidence detection was set to 27 ns which results in a timing window efficiency of 88%. The measured coincident background count rate was 150 cts/s. In order to test the effectiveness of the shielding a 0.77 mCi Ge68 rod source was attached directly to the front shielding. This increased the coincident background count rate by 45 cts/s. The expected additional background coming from the patient activity should be lower due to a larger distance to the detector unit. FIG. 8 shows the count rate for the 0.8 mCi Ge68 point source during warm-up of the detector unit caused by heating from operation of the MR apparatus. The loss of sensitivity is caused by the gain dependency of APDs to temperature variations. The count rate has been corrected for dead time (5 ms per trigger), background, random coincidences and timing window efficiency. The final sensitivity is slightly under 28% for a source in the center of the detector. In this regard, NIM electronics could be replaced by digital pulse processing. This would allow using a suitable algorithm to correct for temperature effects, and thus, avoiding warm-up phases.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A blood sampling system for measuring radioactivity levels in arterial blood of a subject undergoing PET (Positron Emission Tomography) imaging in a combined PET/MR (Magnetic Resonance) apparatus, comprising:
   an MR magnet configured to generate an MR magnetic field;
   at least one PET detector ring having an outer diameter dimensioned to be received within said MR magnet such that said at least one PET detector ring is concentric with said MR magnet, said at least one PET detector ring and MR magnet forming a PET/MR detector assembly;
   a patient bed configured to receive a patient to be imaged, said patient bed being positioned within said PET/MR detector assembly;
   a detector unit including a pair of scintillation crystals;
   gamma ray shielding surrounding said detector unit;
   a solid-state photodetector coupled to each of said crystals;
   a catheter carrying arterial blood from said subject, said catheter passing between said crystals; and
   a signal processing circuit electrically coupled to said solid-state photodetectors to receive scintillation event signals from said photodetectors and to process outside said MR magnetic field said signals for measurement of radioactivity levels in said subject's blood, wherein outputs from said at least one PET detector ring are sampled and digitized outside of the MR magnetic field;
   wherein said detector unit is located in the MR magnetic field produced by said PET/MR apparatus.

2. The blood sampling system of claim 1, wherein said pair of scintillation crystals are made of LSO (lutetium orthosilicate).

3. The blood sampling system of claim 2, wherein said LSO crystals are in the form of blocks.

4. The blood sampling system of claim 1, wherein said solid-state photodetectors are APDs (avalanche photodiodes).

5. The blood sampling system of claim 1, further comprising a MR filter plate through which signals pass from said detector unit to said signal processing unit.

6. The blood sampling system of claim 1, wherein said gamma ray shielding is made of a tungsten polymer composite material.

7. The blood sampling system of claim 1, wherein coincident event triggering of said signal processing circuit is performed by a first crystal absorbing an electron and a second crystal absorbing gamma rays resulting from 8-decay of a background source of said detector unit.

8. A blood sampling system for measuring radioactivity levels in arterial blood of a subject undergoing PET (Positron Emission Tomography) imaging in a combined PET/MR (Magnetic Resonance) apparatus, comprising:
   an MR magnet configured to generate an MR magnetic field;
   a pair of planar PET detector panels positioned within said MR magnet, said pair of planar PET detector panels and MR magnet forming a PET/MR detector assembly;
   a patient bed configured to receive a patient to be imaged, said patient bed being positioned within said PET/MR detector assembly;
   a detector unit including a pair of scintillation crystals;
   gamma ray shielding surrounding said detector unit;
   a solid-state photodetector coupled to each of said crystals;
   a catheter carrying arterial blood from said subject, said catheter passing between said crystals; and
   a signal processing circuit electrically coupled to said solid-state photodetectors to receive scintillation event signals from said photodetectors and to process outside said MR magnetic field said signals for measurement of radioactivity levels in said subject's blood, wherein outputs from said pair of planar PET detector panels are sampled and digitized outside of the MR magnetic field;
   wherein said detector unit is located in the MR magnetic field produced by said PET/MR apparatus.

9. The blood sampling system of claim 8, wherein said pair of scintillation crystals are made of LSO (lutetium orthosilicate).

10. The blood sampling system of claim 9, wherein said LSO crystals are in the form of blocks.

11. The blood sampling system of claim 8, wherein said solid-state photodetectors are APDs (avalanche photodiodes).

12. The blood sampling system of claim 8, further comprising a MR filter plate through which signals pass from said detector unit to said signal processing unit.

13. The blood sampling system of claim 8, wherein said gamma ray shielding is made of a tungsten polymer composite material.

14. The blood sampling system of claim 8, wherein coincident event triggering of said signal processing circuit is performed by a first crystal absorbing an electron and a second crystal absorbing gamma rays resulting from 8-decay of a background source of said detector unit.

* * * * *